United States Patent
Mason

(10) Patent No.: US 6,781,010 B1
(45) Date of Patent: Aug. 24, 2004

(54) NON-PHOSGENE ROUTE TO THE MANUFACTURE OF ORGANIC ISOCYANATES

(75) Inventor: Robert W. Mason, Lake Charles, LA (US)

(73) Assignee: Lyondell Chemical Company, Greenville, DE (US)

( * ) Notice: Subject to any disclaimer, the term of this patent is extended or adjusted under 35 U.S.C. 154(b) by 318 days.

(21) Appl. No.: 09/664,105

(22) Filed: Sep. 19, 2000

(51) Int. Cl.$^7$ .......................................... C07C 263/00
(52) U.S. Cl. ...................................... 560/338; 560/345
(58) Field of Search ................................ 560/338, 345

(56) References Cited

U.S. PATENT DOCUMENTS

| | | | | |
|---|---|---|---|---|
| 3,054,819 A | * | 9/1962 | Barclay et al. | 560/354 |
| 3,190,905 A | * | 6/1965 | Morschel et al. | 560/344 |
| 3,366,662 A | * | 1/1968 | Kober et al. | 560/345 |
| 3,763,217 A | * | 10/1973 | Brill | 560/24 |
| 3,960,914 A | | 6/1976 | Lyons | |
| 4,100,351 A | * | 7/1978 | Romano et al. | 560/24 |
| 4,268,684 A | * | 5/1981 | Gurgiolo | 560/24 |
| 4,611,079 A | | 9/1986 | Merger et al. | |
| 4,713,476 A | | 12/1987 | Merger et al. | |
| 4,851,565 A | | 7/1989 | Merger et al. | |
| 5,155,267 A | | 10/1992 | Faraj | |
| 5,166,414 A | * | 11/1992 | Okawa | 560/345 |
| 5,686,645 A | * | 11/1997 | Faraj | 560/24 |
| 5,705,673 A | | 1/1998 | Rivetti et al. | |

FOREIGN PATENT DOCUMENTS

| | | |
|---|---|---|
| EP | 436 800 A1 | 7/1991 |
| WO | WO 98/56758 | 12/1998 |
| WO | WO 99/47493 | 9/1999 |

* cited by examiner

Primary Examiner—D. Margaret Seaman
Assistant Examiner—Taylor V Oh
(74) Attorney, Agent, or Firm—Brooks Kushman P.C.

(57) ABSTRACT

A phosgene-free process for producing organic isocyanates reacts an organic fomamide with a diorganocarbonate and thermolyzing the reaction product to obtain the corresponding organic isocyanate. Byproducts may be cycled back to the reaction or recycled to produce additional starting materials. The process product organic isocyanates in high yield.

28 Claims, No Drawings

US 6,781,010 B1

NON-PHOSGENE ROUTE TO THE MANUFACTURE OF ORGANIC ISOCYANATES

TECHNICAL FIELD

The present invention pertains to the industrial production of organic isocyanates.

BACKGROUND ART

Organic isocyanates have widespread industrial use. The isocyanates manufactured in the largest volume are the organic di- and polyisocyanates employed in polymer manufacture, particularly in the production of polyurethanes, polyurethane/ureas, polyisocyanurates, and related polymers. However, monoisocyanates are useful as well, particularly as intermediates in the pesticide, pharmaceutical, and fine chemical industries. The term "isocyanate" herein refers to monoisocyanates and to di- and polyisocyanates, unless indicated to the contrary.

Both aryl as well as aliphatic isocyanates are useful. Aryl isocyanates such as 2,4- and 2,6-toluene diisocyanate (TDI) and 4,4'-diphenylmethane diisocyanate (MDI) dominate isocyanate production because of cost considerations, their reactivity profiles, and their use in polyurethane molded and slabstock foam. However, aliphatic isocyanates such as 1,6-hexane diisocyanate and isophorone diisocyanate are particularly useful where high photolytic stability is desired, and where a flexible aliphatic hydrocarbon chain is desired, for example in paints and coatings.

The manufacture of most commercial isocyanates involves reaction of the corresponding primary amine with phosgene to form the carbamoyl chloride followed by thermolysis to the isocyanate. In the process, two molecules of hydrogen chloride are generated for each isocyanate group created. This byproduct, as hydrochloric acid, has limited commercial value. Additionally, the phosgene used in isocyanate production is expensive and quite hazardous. Hence, the industry has long sought viable non-phosgene methods of isocyanate production. A wide variety of such methods have been proposed, but all thus far have significant drawbacks which, with the exception of isophorone diisocyanate production, have prevented their commercial use.

Numerous processes involve condensation reactions with urea or urea precursors to form a variety of ureas and carbamates, often complex mixtures containing oligomeric or even polymeric species as well. The ureas or carbamates are then pyrolyzed to produce the isocyanate. The pyrolysis of O-substituted carbamates is reasonably efficient. However, to be efficient overall, precursor synthesis must be efficient as well.

Typical of processes suggested for manufacture of thermolyzable carbamate isocyanate precursors is the reaction of amines with dialkylcarbonate in the presence of a suitable catalyst. For example, PCT published application WO 99/47493 discloses the reaction of amines with organic carbonates in excess, preferably in the presence of a heterogenous metal based catalyst. However, yields appear to be quite low.

U.S. Pat. Nos. 4,713,476; 4,611,079; and 4,851,565, disclose the co-condensation of aryl or aliphatic di- or polyamines with urea and excess alcohol to produce di- or poly(O-alkyl) carbamates. A variety of substituted ureas and other products are also produced. Some of the byproducts are necessarily recycled back to the process in order to raise the overall efficiency and diminish waste production. Thus, the overall process is complicated and requires numerous separation and purification steps. Nevertheless, such a process is believed currently employed in the production of isophorone diisocyanate (IPDI).

In U.S. Pat. No. 3,960,914, alkyl or aryl fomamides are converted directly to isocyanates in the presence of precious metal catalysts. However, the reaction proceeds with both low yield and low selectivity. Numerous byproducts are also produced. In U.S. Pat. Nos. 5,155,267 and 5,686,645, asymmetric substituted ureas and carbamates are prepared by reaction of a primary formamide with a dialkylamine or an alcohol in the presence of large amounts of Group VIII transition metal catalyst. Although the yields of disubstituted ureas are relatively high, carbamates are produced in only low yields. The large amount of expensive precious metal catalyst is a considerable disadvantage when commodity isocyanate production is contemplated.

It would be desirable to provide a non-phosgene method of producing isocyanates and their direct precursors on an industrial scale, employing readily available starting materials, which produces the desired products in high yield and with efficient recycling of byproducts.

DISCLOSURE OF INVENTION

It has now been surprisingly discovered that organic isocyanates may be obtained directly by the synthesis and thermolysis of the reaction product of the corresponding formamide and a diorganocarbonate. Major byproducts may themselves be thermolyzed to isocyanates or may be recycled to generate additional raw materials. Thus, the overall process is efficient and generates little waste.

BEST MODE FOR CARRYING OUT THE INVENTION

The process of the present invention is directed to the synthesis of organic isocyanates and substituted O-carbamate analogs by the reaction of an organic formamide with a diorganocarbonate. In the specification which follows, terms such as "corresponding amine", "corresponding isocyanate" and like terms pertain to related compounds of the same structure but with different functional groups obtained by reaction of the "corresponding" functional group. Thus, 2,4-toluene diamine (1) is the "corresponding amine" to 2,4-toluene diamine bis(formamide) (2), 2,4-toluene dilsocyanate (3), and 2,4-toluene diamine bis (organocarbamate) (4). These "corresponding" compounds are represented structurally below, from which their chemical relationship may easily be discerned.

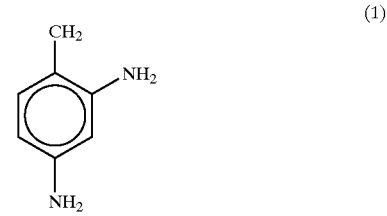

(1)

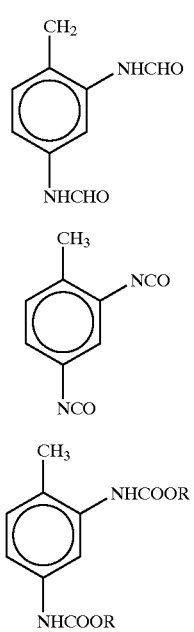

In the overall process of the present invention, a formamide, i.e., (2) generates the corresponding isocyanate (3) as well as a lesser quantity of the corresponding O-organocarbamate (4) which itself may be pyrolyzed to additional isocyanate (3). The amine (1) may serve as a starting raw material for the production of the formamide (2).

The formamides useful in the subject invention are aliphatic and aryl formamides with at least one formamide group. While there is no theoretical upper limit to the number of formamide groups, it is preferable that the starting formamide contain from 1 to 10 formamide groups, more preferably 1 to 5, and most preferably 2 to 4 formamide groups. Mixtures of compounds such as the formamides of polymethylenepolyphenylenepolyamines having structure

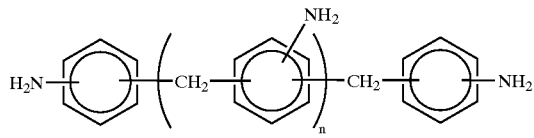

where n is 0 to 10 or higher are useful, for example. In such mixtures, the largest population of molecules are those with values of n from 0 to 4, with n=0 and n=1 generally predominating.

Thus, the formamides preferably correspond to the formula

where n is an integer of at least 1, preferably in the range of 1 to 10, more preferably in the range of 1–5, and most preferably in the range of 2–4.

The organo group R may be any organic group to which the formamide groups may be bound in a stable fashion such that they may be handled in an industrial setting. Non-limiting organo groups R include aryl groups; alkaryl groups; aralkyl groups; linear, branched, and cyclic aliphatic groups, both saturated and unsaturated; and any of the foregoing groups substituted with non-interfering substituents or having ring or chain interspersed heteroatoms. By "non-interfering" is meant that the substituents (or heteroatoms) should not participate unduly in the reaction with diorganocarbonate unless this reaction is desired. Modest reaction which does not substantially impede recovery of the desired product can be tolerated.

Non-limiting examples of suitable substituents include cyano; alkoxy, preferably $C_{1-4}$ alkoxy and more preferably methoxy; halo, particularly chloro and fluoro; halogenated alkyl, i.e., trifluoromethyl, hexafluoropropyl and heptafluoropropyl; nitro; alkylthio; acyl, preferably $C_{1-4}$ lower acyl (—C(O)—R), and the like.

Also suitable for organo groups R are the various silanes and siloxanes, including oligomeric and polymeric species thereof, in which the formamide groups are not bound directly to silicon, but are bound to a hydrocarbon group. A non-limiting example is the compound

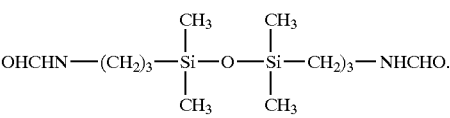

The aryl groups described previously may be heteroaryl, i.e., pyridyl, quinolyl, etc., and the aliphatic hydrocarbons, as stated previously, may also contain heteroatoms, i.e. the bis(formamide) of 1,7-diamino-3-(oxa)heptane. In general, hydrocarbons having —NH— groups interspersed in the aliphatic or cycloaliphatic chain should be avoided due to their potential reactivity in the subject process. However, some —NH— group-containing compounds may be suitable, either because the —NH— groups are less reactive due to electronic or steric factors, because the reaction products can be tolerated in the amounts produced, or because the reaction of the formamide groups is rapid enough that few if any —NH— groups react. The overall principle here is that the reactivity of any substituents or intervening heteroatoms or other groups such as keto groups should not be such that the desired product cannot be obtained. It would not interfere with obtaining a desired product, for example, if the formamide were also to bear thermolyazble substituted urea or carbamate groups, for example. Thus, a compound bearing an O-alkylcarbamate group as well as one or more formamide groups could serve as a suitable formamide raw material.

The formamide starting materials are preferably those in which R is $C_{1-20}$ aliphatic, $C_{4-20}$ cycloaliphatic, $C_{6-20}$ aryl, $C_{7-30}$ aralkyl, and $C_{7-30}$ alkaryl, all optionally substituted with cyano, $C_{1-4}$ alkoxy, perfluoroalkyl, chloro, and fluoro. More preferably, R is substituted or preferably unsubstituted $C_{1-20}$ alkyl, $C_{2-20}$ alkenyl, $C_{2-20}$ alkynyl, $C_{4-20}$ cycloalkyl, $C_{4-20}$ cycloalkenyl, $C_{6-30}$ aryl, $C_{7-30}$ aralkyl or $C_{7-30}$ alkaryl. Most preferably, the starting formamides are those where the formamide groups are attached directly to an aryl ring. Preferred aryl formamides are the formamides of aryl amines such as aniline, 2-, 3-, and 4-methylaniline; 1,2-, 1,3-, and 1,4-phenylene diamine; the various toluene diamines, particularly 2,4-, 2,6-, and 3,5-toluene diamines; the various diaminodiphenylmethanes, particularly 2,2'-, 2,4', and most preferably 4,4'-diaminodiphenylmethane; other diaminodiphenyl compounds such as the various diaminodiphenylsulfones, diaminodiphenyloxides, diaminodiphenylsulfides, and the like. In all of the foregoing aliphatic, cycloaliphatic, aryl, etc. compounds, the various basic structures may be hydrocarbon substituted, preferably by one or more alkyl, aryl, or heteroaryl groups. It has been surprisingly discovered that exceptional yields of isocyanate and isocyanate precursors may be obtained without the use of catalysts, when aryl formamides are employed. Catalyst-free processes are preferred, especially when cost is a consideration.

The diorganocarbonates useful include any diorganocarbonates which provide suitable reactivity. Cyclic carbonates such as propylene carbonate may also be useful. The diorganocarbonate may be chosen for its relative ease or difficulty of separation from the reaction mixture. For example, with volatile isocyanate products, a high boiling organocarbonate may be chosen, whereas for non-volatile isocyanates, a low boiling organocarbonate may be employed. The organocarbonates conform to the structure

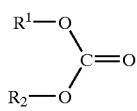

where $R^1$ and $R^2$ may be the same or different, and may be substituted or unsubstituted aliphatic, cycloaliphatic, aryl, arylalkyl, or alkaryl groups, or together may constitute a cyclic structure. It is most preferable that a diorganocarbonate which is commercially available or which may be readily and economically synthesized be employed. Suitable diorganocarbonates include, but are not limited to dimethylcarbonate, diethylcarbonate, di(n-propyl) carbonate, di(n-bexyl)carbonate, di(2-ethylhexyl)carbonate, diphenylcarbonate, di(4-chlorophenyl)carbonate, and the like. Additional carbonates are disclosed in U.S. Pat. No. 3,366,662 at column 2, lines 37–43 and WO 99/97493, page 2, line 17 to page 3, line 2, which are incorporated herein by reference. A particularly reactive but less accessible carbonate is di-(4-nitrophenyl) carbonate. Most preferred is diphenylcarbonate when a high boiling carbonate is employed. Mixed carbonates such as aliphatic/aryl- and cycloaliphatic/aryl-carbonates are also quite useful, and also preferred. An example is methylphenylcarbonate. Methylphenylcarbonate can be produced by the process disclosed in U.S. Pat. No. 5,705,673.

The reaction may take place neat or in the presence of a solvent. The reaction may also take place at ambient pressure, or at lower or higher pressure. In general, the pressure and temperature may be adjusted so as to obtain both high yield and efficient purification. With diphenylcarbonate as the diorganocarbonate, phenol may be employed as a solvent when volatile isocyanates are produced, for example. Solvents which aid in stripping off isocyanate and/or carbonate or form azeotropes therewith may also be used. Preferably, such solvents are relatively inert, toluene being a suitable choice in some preparations.

The particular reaction conditions can be varied widely to take into account such parameters as the reactivity of the formamide starting material, the ease of thermolysis of the formamide/diorganocarbonate reaction products; the volatilities of the isocyanates, carbamates, and mixed isocyanate/carbamate products obtained, the volatility of the byproduct formate esters obtained, and the like. All such parameters are within the skill of the art to determine and optimize.

The overall reaction scheme may be set forth below, as illustrated by the preparation of 2,4-toluene diisocyanate.

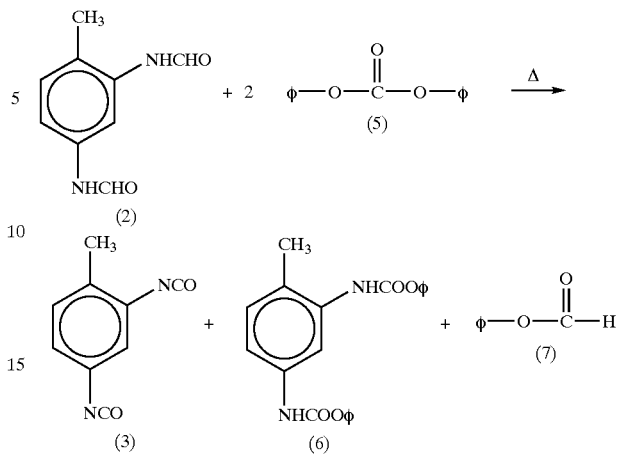

Byproducts are generated, as expected. However, the amounts of byproducts generated are small. It is expected that in addition to the bis(carbamate) product, that mixed isocyanate/carbamate products such as

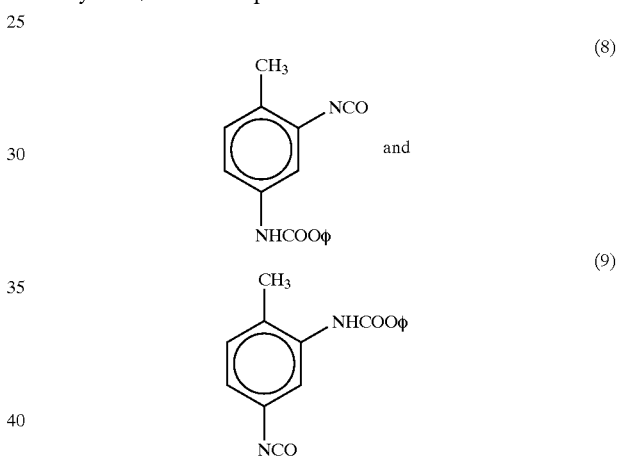

will also be generated. All the carbamate-containing species (6,8,9) may be easily thermolyzed to the corresponding diisocyanate (3). This thermolysis is believed to be the major route to the isocyanates produced in the process. In semi-batch or continuous processes, the thermolysis of carbamate-containing products will continue as the reaction progresses, and although a steady state finite carbamate concentration will be maintained, the overall carbamate production over time can be reduced to very low values. The carbamates and mixed isocyanate/carbamates may be separated and separately thermolyzed to isocyanates if desired.

The formate ester product, here phenol formate, can be used to regenerate formamide starting material:

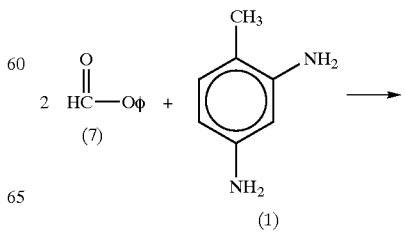

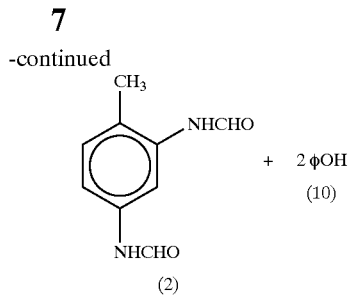

The phenol obtained may be recycled in an integrated process to produce diphenylcarbonate, or may be sold, as it has significant commercial value. When lower alkylcarbonates are employed, the alkanols reclaimed may be sold, recycled, or employed as fuel. Overall, the process generates little in the way of waste which must be landfilled, incinerated, or otherwise disposed of.

The reaction between the organic formamide and diorganocarbonate may also proceed while generating the formamide in situ. In such processes, the corresponding amine and an organoformate are reacted with diorganocarbonate. The organo group of the organoformate may be the same or different from the organo group(s) of the diorganocarbonate, but is preferably the same as at least one of the two diorganocarbonate organo groups for ease of product separation. The ratio of organoformate to the corresponding amine (the amine corresponding to the desired isocyanate) is preferably 0.5 mol per mol of amino groups or more, more preferably 1.0 mol or more per mol of amino groups, and most preferably in the range of 1.0 to 5.0 mol per mol of amino groups. A ratio of 1.5:1 has been found suitable, for example, but larger ratios are tolerable, particularly when the organoformate is easily separable from the isocyanate product. With appropriate recycling in a continuous process, lower ratios may be suitable as well.

It is unknown whether the amine and organoformate initially react to form the corresponding carbamide which then reacts with diorganocarbonate, or whether some other reaction pathway is operable. A concerted reaction is possible although not likely. In the present application and in the claims, unless indicated otherwise, the term "its amine and formate precursors" refer to a mixture of the corresponding amine and a formate. For purposes of illustration, the amine and formate precursors of the bis(formamide) of 2,4-toluene diamine are 2,4-toluene diamine and a formate ester, i.e. phenylformate.

The temperature of the process may be adjusted so as to supply the requisite product, or to enable efficient separation of product(s), or both. For example, if the desired product is a carbamate isocyanate precursor such as a biscarbamate of 2,4-toluene diamine, the reaction should take place at a temperature at which substantial thermolysis of the carbamate to the isocyanate is avoided, for example below 190° C., and preferably below 150° C. The onset of thermolysis is substrate dependent, and for any given carbamate is determined easily, for example by differential scanning calorimetry (DSC). If the predominate product is desired to be an isocyanate, temperatures in excess of 150° C. and preferably in excess of 190° C. are employed. Temperatures in the range of 190° C. to 220° C. are particularly useful. In the production of isocyanates in particular, a reaction temperature lower than optimal for the carbamate to isocyanate thermolysis may be employed if such lower temperature will aid in separation of gaseous reaction products. The thermolysis of the reaction mixture of the bis(formamide) of 4,4'-diaminodiphenylmethane and diphenylcarbonate begins to produce isocyanate product at about 150° C., while the analogous reaction employing the bis(formamide) of 2,4-toluene diamine does not begin significant thermolysis until 190°–200° C. For aryl isocyanate production, thermolysis onset ordinarily occurs within the range of 150° C. to 240° C. However, higher and lower temperatures may be used as well. The reactions under these conditions are generally run under vacuum to facilitate removal of phenol, phenol formate and isocyanate. However, the reaction may be successfully run at atmospheric temperature or at superatmospheric pressure. Phenol may be recycled back to the reaction mixture.

The ratio of diorganocarbonate to formamide on a mol diorganocarbonate to mol formamide group basis is preferably greater than 0.5:1, more preferably at least 1:1, yet more preferably in the range of 1.5 to 20:1, and most preferably about 2:1 to 5:1. Ratios of 2:1 to 4:1 have been found very suitable. The low ratios such as 2:1 and 4:1 at which high yields may be obtained make the subject invention more attractive than reactions between organic amines and diorganocarbonates which, in addition to producing low yields of isocyanate, have required high (10:1) diphenylcarbonate/amine ratios to generate even these low yields.

When aliphatic or cycloaliphatic formamides are employed, preparation of the corresponding carbamide, carbamide/isocyanate, or isocyanate may require catalysis. Suitable catalysts are metal catalysts such as the various transition metal and regular group metal salts, complexes, and organometallic compounds which are useful in catalyzing carbamate thermolysis. Transesterification and transurethanation catalysts such as copper, tin, and zinc salts are useful, for example. See U.S. Pat. No. 4,851,565, for example, at column 6, line 19 to column 7, line 7, herein incorporated by reference. Catalysis may be used with aryl formamides as well.

Having generally described this invention, a further understanding can be obtained by reference to certain specific examples which are provided herein for purposes of illustration only and are not intended to be limiting unless otherwise specified.

EXAMPLE 1

Diphenyl carbonate (33.2 grams, 0.155 mole) is charged to a 50 ml three-neck flask equipped with a magnetic stirbar, a six inch Vigreaux column topped with a short path distillation head and an electrically heated addition funnel charged with a solution of formanilide (4.69 grams, 0.039 mole) in molten phenol (16.56 grams, 0.176 mole). The diphenyl carbonate is heated to 213° C. at 100 mmHg vacuum and the phenol/formanilide mixture added dropwise over a 50 minute period. When the addition is complete, the vacuum is slowly lowered to 5 mmHg over the next 10 minutes to remove the remaining phenol and phenyl isocyanate from the remaining diphenyl carbonate. Internal standard gas chromatographic (IS/GC) analysis of the overhead (29.72 grams) and pot material (22.94 grams) shows production of 4.17 grams of phenyl isocyanate and 0.02 grams of phenyl isocyanate as phenol carbamate, as a solution in phenyl formate and phenol, a recovery of 0.0352 moles of phenyl isocyanate (91.0% yield, based on formanilide fed). In calculating the yield of isocyanate, the easily thermolyzed carbamate is considered as isocyanate.

EXAMPLE 2

The di-formamide of 2,4-toluene diamine is prepared by either reaction of the diamine with formic acid, with azeotropic removal of water with refluxing toluene, or by reaction of the diamine with phenyl formate in phenol. As in Example 1 above, the di-formamide (5.46 grams, 0.0307 mole) in phenol (17.50 grams, 0.186 mole) is added dropwise to diphenyl carbonate (26.40 grams, 0.123 mole) and heated to 232° C. at 110 mmHg. IS/GC analysis of the overhead (30.55 grams) and pot material (17.42 grams) shows the recovery of 4.004 grams of free 2,4-TDI and 0.277 grams of 2,4-TDI as phenol carbamate (0.0246 moles total TDI, 79.9% yield, based on di-formamide fed).

EXAMPLE 3

A mixture of 15.69 grams, 0.0881 mole of 2,4-toluene-diformamide, containing an additional 0.04 grams of phenol, and 143.16 grams, 0.6684 mole of diphenyl carbonate is heated, with magnetic stirring, to reflux at 160 mmHg. Distillation commenced at 212° C. pot, 143° C. distillate temperature and is terminated 35 minutes later at 237° C. pot and 196° C. distillate temperature. The 40.55 grams of distillate contains 4.072 grams of TDI, while 10.506 grams of 2,4-TDI remains in the 117.62 grams of pot material, a total recovery of 14.578 grams of 2,4-TDI, 0.838 mole, for a diformamide to diisocyanate yield of 95.1%.

EXAMPLE 4

To a 5 ml vial is added (2.00 grams), 2,4-toluene-diformamide (0.458 grams, 2.57 mmole) and methylphenyl-carbonate (1.56 grams, 10.26 mmole). The solution is heated to 199° C. with stirring. Complete conversion of the diformamide to 2,4-toluene diisocyanate-bis (methanolcarbamate) occurs within 45 minutes. Anisole was formed as a byproduct.

EXAMPLE 5

The di-formamide of 4,4'-methylene-dianiline is prepared by the reaction of the diamine with 2.1 molar equivalents of formic acid, and removing the water byproduct by azeotropic distillation with toluene. Using the same apparatus as Example 1, but without the addition funnel, diphenyl carbonate (48.45 grams, 0.226 mole) and 4,4'-MDA-di-formamide (6.92 grams, 0.0272 mole), containing 0.21 grams of phenol, is heated to reflux at 38 mmHg. Reaction and phenol/phenyl formate distillation commences at a pot temperature of 155° C., and ceases 30 minutes later at a pot temperature of 195° C., 17 mmHg. IS/GC analysis of the condensate (10.55 grams) shows only phenyl formate, phenol and a trace of DPC. The pot material (43.97 grams) contains 3.02 grams of 4,4'-diphenylmethane diisocyanate (MDI) and 3.21 grams of MDI as the mono-phenol carbamate, a recovery of 0.0249 mole equivalents of MDI, equal to a 91.6% yield, based on di-formamide charged.

The high yield of isocyanate and easily thermolyzable carbamate is noteworthy, typical yields being higher than 80%, and often higher than 95%. These processes have not been optimized. Also noteworthy is the ability to employ low mol ratios of diorganocarbonate to formamide. In Example 2, for example, the mol ratio is 2:1, yet a yield of 79.9% is obtained. Example 5 illustrates a procedure where the product is retained in the reaction mixture rather than separated as an overhead. Example 4 shows that when conducted at low temperature, the non-thermolyzed carbamate may be obtained in high yield.

EXAMPLE 6

A mixture of 3.12 grams, 0.0256 mole of 2,4-toluene diamine, 9.62 grams, 0.0789 mole of phenyl formate (Fluka) and 22.26 grams, 0.1039 mole of diphenyl carbonate is warmed to reflux under a nitrogen atmosphere, with magnetic stirring. The reaction mixture temperature increases from 188° C. to 200° C. over a 60 minute period. IS/GC analysis of the final, clear pot solution indicates the presence of 3.682 grams, 0.0212 moles of 2,4-toluene diisocyanate, a yield of 82.7%.

EXAMPLE 7

A mixture of 153.10 grams, 0.715 mole of diphenyl carbonate and 17.85 grams, 0.094 mole of the formamide of 3,4-dichloroaniline (prepared by the reaction of the amine and formic acid) is magnetically stirred and heated at 160 mmHg. The pot temperature reaches 222° C., then drops slightly to 218° C. as phenol and phenyl formate began to distill over at 145C. Distillation is terminated 33 minutes later at a pot temperature of 236° C. and a distillate temperature of 191C., collecting 23.86 grams of distillate, with 146.41 grams remaining in the pot. IS/GC analysis indicates the presence of 2.464 grams of 3,4-dichlorophenyl isocyanate in the distillate and 13.127 grams in the pot, a total of 15.591 grams, 0.0829 mole, a yield of 88.2%.

EXAMPLE 8

A mixture of 64.18 grams, 0.299 mole of diphenyl carbonate and 5.13 grams, 0.0298 mole of the diformamide of 1,6-hexamethylene-diamine (prepared by the reaction of the diamine with formic acid) is magnetically stirred and heated under a nitrogen atmosphere. Boiling commences at 198° C. and continues for 60 minutes, when the pot temperature peaks at 242° C. IS/GC analysis of the final, clear pot solution indicates the presence of 2.225 grams, 0.0132 mole of free 1,6-hexamethylene-diisocyanate (44.4% yield), with the remainder of the HDI equivalent present in solution as the phenol carbamates.

Example 6 illustrates that reaction of the corresponding formamide itself is not necessary; the formamide precursors, i.e. the corresponding amine and a formate, in this case, phenyl formate, may serve as the raw materials, either generating the formamide in situ or involving an unknown reaction pathway to generate isocyanate in high yield. Example 7 illustrates reaction of a substituted aryl formamide, while Example 8 illustrates reaction of an aliphatic formamide. Although the yield of isocyanate is lower in Example 8 than with aryl formamides, the reaction mixture contains large amounts of thermolyzable phenol carbamates. This example is non-catalyzed. A catalyzed reaction is expected to produce higher direct yield of the corresponding isocyanate.

Having now fully described the invention, it will be apparent to one of ordinary skill in the art that many changes and modifications can be made thereto without departing from the spirit or scope of the invention as set forth herein.

What is claimed is:

1. A process for the preparation of organic isocyanates, said process comprising:
   a) forming a reaction mixture by mixing an organic formamide compound or its amine and formate precursors with at least one diorganocarbonate selected from the group consisting of diarylcarbonates, mixed aliphatic/aryl-carbonates and cycloalphatic/aryl-carbonates;
   b) subjecting said reaction mixture to an elevated temperature sufficient to generate the isocyanate corresponding to said organic formamide compound; and
   c) isolating said isocyanate from said reaction mixture;

wherein said organic formamide compound is one of the formula

where n is an integer from 1 to 10 and R is an organic radical.

2. The process of claim 1, wherein said organic formamide compound is one of the formula

where n is an integer from 1 to 10 and R is an organic radical.

3. The process of claim 2, wherein R comprises an optionally substituted $C_{1-20}$ alkyl, $C_{2-20}$ alkenyl, $C_{2-20}$ alkynyl, $C_{4-20}$ cycloalkyl, $C_{4-20}$ cycloalkenyl, $C_{6-30}$ aryl, $C_{7-30}$ aralkyl, $C_{7-30}$ alkaryl group, a silane or siloxane or oligomer thereof wherein formamide group(s) are bound to an Si—C-bonded hydrocarbon group, and wherein each of the above R may contain one or more chain or ring heteroatoms.

4. The process of claim 2, wherein R is selected from the group consisting of optionally substituted phenyl, diphenylmethane, and tolyl groups.

5. The process of claim 4, wherein R is the 2,4-bis(N-formamide) of toluene diamine.

6. The process of claim 1, wherein steps a) and b) are combined such that the reaction temperature of step a) is maintained at a temperature wherein isocyanate is produced directly without prior isolation of O-organocarbamate from said reaction mixture.

7. The process of claim 6, wherein the temperature of steps a) and b) are in the range of 150° C. to 240° C.

8. The process of claim 1, wherein the temperature of step a) is maintained below 190° C. and at a first temperature such that no substantial production of isocyanate occurs, said process further comprising:
  a)i) isolating an intermediate, isocyanate precursor mixture containing a carbamate group-containing reaction product, and thermolyzing said isocyanate precursor mixture at a second, higher temperature to obtain the isocyanate corresponding to said organic formamide.

9. The process of claim 8, wherein said isocyanate precursor reaction mixture comprises in excess of 80 mol percent of the carbamate corresponding to said organic formamide, said mol percent based on the total of mols of isocyanate, carbamates and isocyanate/carbamate contained in said isocyanate precursor reaction mixture.

10. The process of claim 1, wherein said diorganocarbonate is a diarylcarbonate.

11. The process of claim 1, wherein said diorganocarbonate is diphenylcarbonate.

12. The process of claim 2, wherein R is aliphatic or cycloaliphatic, said process further comprising adding to said reaction mixture a metal catalyst which is effective to accelerate cleavage of carbamates produced by said process.

13. The process of claim 1, wherein the ratio of mols of diorganocarbonate to organic formamide is greater than 1:1 based on mols of formamide groups.

14. The process of claim 1, wherein the ratio of mols of diorganocarbonate to mols of formamide groups is 2:1 to 5:1.

15. The process of claim 1, wherein no catalyst is present.

16. The process of claim 1, wherein one or more organic di- or polyamines, an organoformate ester, and diorganophenol carbonate comprise said reaction mixture.

17. The process of claim 16, wherein said organo group of said organoformate is the same as at least one of the organo groups of said diorganocarbonate, said organo groups selected from the group consisting of $C_{1-20}$ aliphatic, $C_{4-20}$ cycloaliphatic, $C_{6-20}$ aryl, $C_{7-30}$ aralkyl, and $C_{7-30}$ alkaryl groups, their heteroatom substituted analogs, and mixtures thereof.

18. The process of claim 16, wherein said organo groups are selected from the group consisting of $C_{1-20}$ alkyl, $C_{5-8}$ cycloalkyl, and optionally substituted $C_{6-10}$ aryl.

19. The process of claim 16, wherein all organo groups are phenyl.

20. The process of claim 16, which is a continuous process wherein organoformate is removed from said reaction mixture and recycled to said reaction mixture with additional organic di- or polyamine.

21. A process for the direct manufacture of an organic isocyanate from the corresponding formamide, said process comprising:
  a) reacting an organic formamide containing from 1 to 10 formamide groups per molecule with from 1 to about 10 mol of diorganocarbonate per mol of formamide groups to form a reaction mixture, said reacting taking place at a temperature such that themolysis of products contained in said reaction mixture generates the isocyanate corresponding to said organic formamide;
  b) separating said isocyanate from said reaction mixture.

22. The process of claim 21, wherein said isocyanate separated from said reaction mixture also contains partially thermolyzed products containing carbamates corresponding to said organic formamide and/or mixed isocyanate/carbamide compounds corresponding to said organic formamide, said process further comprising:
  b)i) further thermolyzing said partially thermolyzed products to form additional isocyanate corresponding to said organic formamide; or
  b)ii) returning said partially thermolyzed products to said reaction mixture; or
  b)iii) performing both of b)i) and b)ii).

23. The process of claim 21, wherein diphenylcarbonate is employed as said diorganocarbonate, reaction takes place in phenol solvent, and said isocyanate separated from said reaction mixture contains phenol and phenol formate ester, said process further comprising recycling said phenol formate ester by reacting said phenol formate ester with an organic amine corresponding to said organic formamide to form said organic formamide.

24. The process of claim 21, wherein said organoformate has a boiling point above the decomposition temperature of the O-organocarbonate corresponding to the organic formamide.

25. A continuous process for producing organic isocyanates, said process comprising:
  a) reacting an aryl di- or polyformamide or an amine and formate precursor thereof, with diphenyl carbonate at a temperature at least sufficient to form a reaction mixture containing O-phenylcarbamates corresponding to said aryl di- or polyformamide;
  b) thermolyzing all or a portion of said reaction mixture to generate an isocyanate-containing mixture comprising organic isocyanate(s) corresponding to said aryl di- or polyformamide;
  c) separating said organic isocyanate from said isocyanate-containing mixture to obtain a purified organic isocyanate, and an organic isocyanate depleted mixture c)i);
  d) separating phenol from said isocyanate-containing mixture or from said organic isocyanate-depleted mixture to form a phenol-depleted mixture d)i);

e) separating carbamates and carbamate/isocyanates from said isocyanate-containing mixture or from said mixture c)i), or d)i) and further processing said carbamates and carbamate/isocyanates by one or both of
   e)i) further thermolyzing to form said organic isocyanate(s) corresponding to said aryl di- or polyformamide; or
   e)ii) cycling said carbamates and/or said carbamate/isocyanates into said reaction mixture of step a),
to form a carbamate-depleted mixture e)iii
f) separating from one or more of said isocyanate-containing mixture, c)i, d)i), or e)iii) phenol formate ester, and
g) optionally reacting said phenol formate ester with an organic amine to form the formamide corresponding to said organic amine.

26. The process of claim 25, wherein said step of thermolyzing takes place at a temperature of from 150° C. to 240° C.

27. A process for the preparation of an O-organocarbamate, said process comprising reacting an organic formamide or its amine and formate precursors with a diorganocarbonate at a temperature below that at which significant thermolysis of O-organocarbamate to isocyanate occurs, and separating said O-organocarbamate from other reaction products.

28. The process of claim 1, wherein said organic formamide compounds is one of formula

wherein n is from 1–5 and R comprise $C_{6-30}$ aryl, or a formamide of the structure

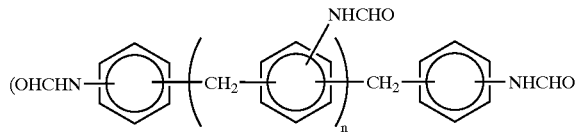

wherein n is from 0 to 3.

* * * * *

UNITED STATES PATENT AND TRADEMARK OFFICE
CERTIFICATE OF CORRECTION

PATENT NO. : 6,781,010 B1
DATED : August 24, 2004
INVENTOR(S) : Robert W. Mason

It is certified that error appears in the above-identified patent and that said Letters Patent is hereby corrected as shown below:

<u>Title page</u>,
Item [73], Assignee, delete "Lyondell Chemical Company" and insert therefor
-- Arco Chemical Technology L.P. --.

<u>Column 11</u>,
Lines 13, 21 and 52, delete "2" and insert therefor -- 1 --.

Signed and Sealed this

Eleventh Day of January, 2005

JON W. DUDAS
*Director of the United States Patent and Trademark Office*

Disclaimer

6,781,010 B1 — Robert W. Mason, Lake Charles, LA (US), NON-PHOSGENE ROUTE TO THE MANUFACTURE OF ORGANIC ISOCYANATES. Patent dated Aug. 24, 2004. Disclaimer filed Oct. 15, 2004, by the assignee, Lyondell Chemical Company.

Hereby enter this disclaimer to claim 2 of said patent.

*(Official Gazette, April 22, 2008)*